United States Patent [19]

Faunce

[11] Patent Number: 4,475,892
[45] Date of Patent: Oct. 9, 1984

[54] MICROCELLULAR CERAMIC MATERIAL AND PROCESS FOR MANUFACTURE THEREOF

[75] Inventor: Frank R. Faunce, Muncie, Ind.

[73] Assignee: Jaff Investment Company, Muncie, Ind.

[21] Appl. No.: 434,067

[22] Filed: Oct. 13, 1982

[51] Int. Cl.³ ............................................. C09K 3/00
[52] U.S. Cl. .................................. 433/212; 433/228; 106/35; 428/392; 428/294; 428/296
[58] Field of Search .................. 106/35; 433/228, 212; 428/293, 294, 295, 392

[56] References Cited

U.S. PATENT DOCUMENTS

| | | | |
|---|---|---|---|
| 3,796,627 | 3/1974 | Maizocchi | 428/294 X |
| 3,869,335 | 3/1975 | Siefert | 428/294 |
| 4,248,936 | 2/1981 | Maizocchi et al. | 428/392 X |
| 4,250,221 | 2/1981 | Pfeffer | 428/293 X |
| 4,278,630 | 7/1981 | Scheicher | 264/60 |
| 4,321,042 | 3/1982 | Scheicher | 433/201 |

*Primary Examiner*—George F. Lesmes
*Assistant Examiner*—Nancy A. B. Swisher
*Attorney, Agent, or Firm*—James L. Jackson

[57] ABSTRACT

Microcellular ceramic material comprises a plurality of elongated vitreous micro sized ceramic rods which are placed in side-by-side touching relation and define elongated lines of contact therebetween. The rods also define interstices therebetween which may be void or may be filled or substantially filled with vitreous fibers, polymer materials, acid soluble or insoluble vitreous fibers and other suitable fibers. The rod mass either so filled or unfilled is first fused at the lines of rod contact by elevated temperature and is then annealed to cause the ceramic fibers to crystallize and form an elongated porous crystalline log. The log is then sectioned transversely or linearly to form thin wafers which in turn are built up in layers which are fused to form useful integral composite cellular objects. Through use of selectively arranged colored fibers the transversely sectioned wafers will have controlled microdots of color to provide the object with controlled color characteristics. Where polymer material is employed to fill the interstices, it may contain color pigments to achieve desired color characteristics.

15 Claims, 10 Drawing Figures

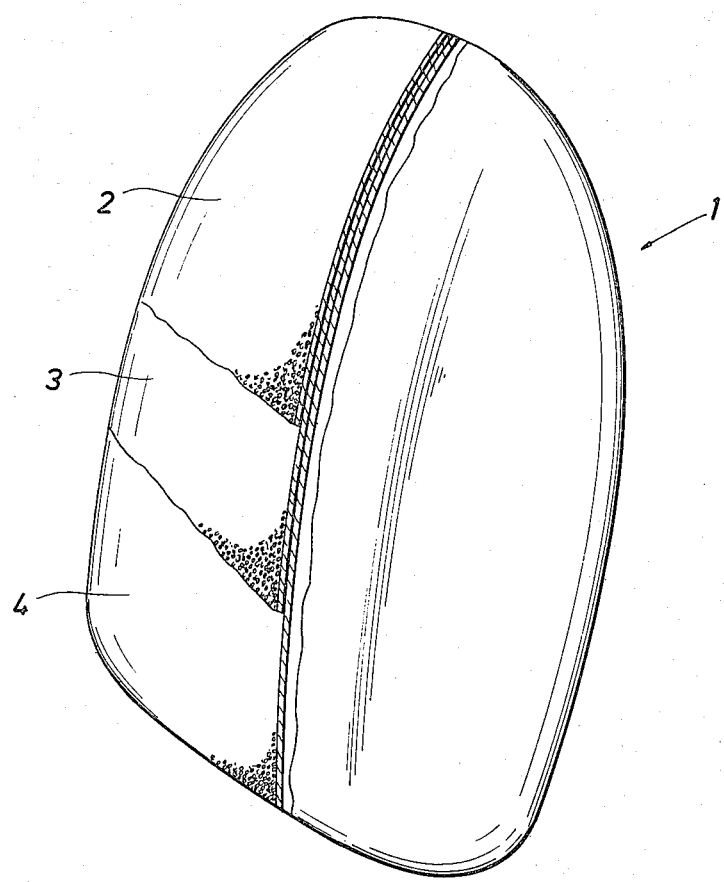
FIG.1
FIG.2
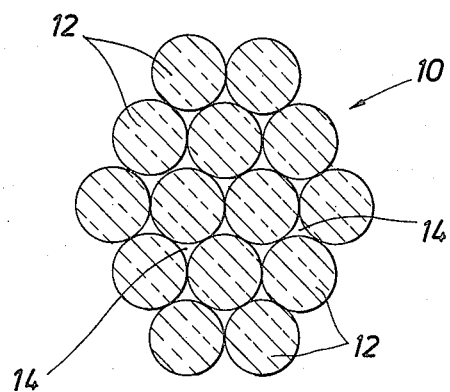
FIG.3
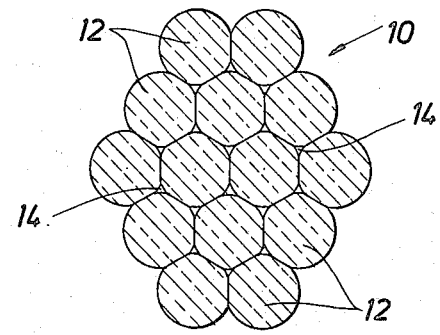
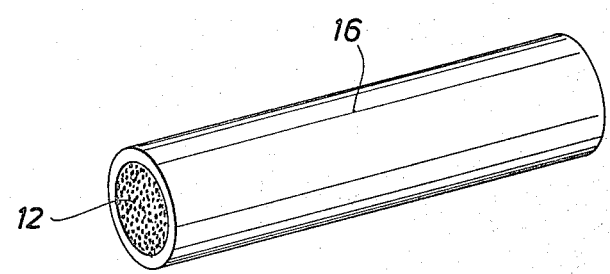
FIG.4

MICROCELLULAR CERAMIC MATERIAL AND PROCESS FOR MANUFACTURE THEREOF

FIELD OF THE INVENTION

This invention relates generally to energy absorbing and impact resistant ceramic materials which find efficient uses to biological fields such as medicine and dentistry and which also find wide use in general mechanical fields. More specifically, the present invention relates to a microcellular ceramic material which may be employed in the dental industry for uses such as in dental veneers, crown, caps and other dental restorations and as bone substitutes such as for dental prosthesis such as in the case of the tempero-mandibular joint. In the medical field, microcellular ceramic material finds efficient uses in the manufacture of bone prosthesis such as hip joints, vertebrae, knuckles, skull bone, and long bones such as in the arms and legs of human and animal subjects. Microcellular ceramic materials also find efficient uses in mechanical structures such as in the case of energy absorbing devices, structural materials with or without integrated electrical circuitry, vehicle skin structure which may incorporate electrical circuitry, etc.

BACKGROUND OF THE INVENTION

Although the present invention finds efficient uses in a wide range of biological, mechanical and electromechanical structures, for the purpose of efficient understanding hereof, this invention is discussed particularly as it pertains to biological fields such as in medicine and dentistry. In the dental industry, certain nonmetal dental prosthesis such as caps, crowns, pontics, etc., are manufactured from ceramic materials. Traditionally, the crowns or caps that are placed over prepared teeth are composed of an amorphous ceramic material that its built up by hand with powdered ceramic material and then fused in a high temperature oven either by one, two or three bakings at various temperatures to cause fusion of the silicon or glass materials. This is a very time consuming and painstaking process that requires a great deal of artistic skill on the part of the technician or ceramist. The requirement for a time consuming and painstaking process together with artistic skill of significant character greatly increases the cost of caps and crowns and other similar prosthesis. The technician or ceramist must be quite knowledgeable from the standpoint of color matching techniques in order to achieve development of a restoration of aesthetic quality. It is desirable therefore to provide an efficient method for manufacturing dental veneers, crowns, caps and other dental prosthesis which may be formed by a simplified manufacturing process and with a minimal of skilled labor and yet provide a resulting aesthetic restoration of optimum quality. It is also desirable to provide a preformed crown or cap structure which could be placed into an appropriate mold to form the crown or cap utilizing a fusion technique that would provide a tooth-like structure having the outward appearance of an aesthetic restoration without all the problems of color matching or technical training on the part of the technician involved in the manufacturing process. The cap or crown structure could be prefabricated to a general form and then molded to the precise shape and structural configuration of a prepared tooth in a controlled temperature furnace under either pressure or vacuum.

In the case of medical structures as prosthesis devices for replacement of bones and bone structure, ceramic materials are seldom employed because by nature such materials are generally of amorphous character and thereby lack energy absorbing capability that is necessary in bones. Moreover, bones have a microcellular or trabecular structure which renders them flexible and yet provides them with exceptional strength in both compression and tension. Heretofore, it has not been possible to provide medical prosthesis devices which have a cellular or trabecular structure and a strength-to-weight ratio which compares favorably with the structure of human bone. It is therefore desirable to provide a microcellular ceramic material having a microcellular structure which closely resembles the cellular trabecular structure of bone and which provides efficient bone-like strength-to-weight ratio as well as providing exceptional strength in compression, tension and bending.

Polymer materials such as polymethylmethacrylate and the like are typically employed in the manufacture of dental veneers. Such polymer materials, though finding wide acceptance, have a number of limiting factors that require improvement in order to render them acceptable for extended use in the oral environment. Although polymer materials may be colored for tooth-like appearance they typically lack the color depth and slight translucency of natural teeth. Further, the color systems of polymer dental veneers tend to degrade after extended use in the oral environment so that the veneers begin to lose their natural appearance. These materials also tend to reflect unusual color characteristics when exposed to certain wavelengths of light, thereby giving the teeth of the patient an unnatural color under some circumstances. Even more disadvantageous, polymer dental materials used for dental veneers tend to become stained and discolored after extended use especially where the patient smokes tobacco products, drinks tea and coffee or consumes certain food products having stains to which the polymers are susceptible. It is desirable therefore to provide dental laminate veneers and other dental prosthesis which resist staining, are more wear resistant than polymer veneers and which have permanent, nondegrading color systems that provide a normal tooth-like color and appearance.

THE PRIOR ART

U.S. Pat. Nos. 3,936,939 and 3,986,261 relate to the present invention only to the extent that they cover dental laminate veneers. The subject matter of patent application Ser. No. 361,257 of Frank R. Faunce, filed Mar. 24, 1982, and entitled "Composite Laminate Dental Veneer and Color System Therefor" is directed to color systems of additive and subtractive nature for laminate vveneers and also discuss polarization of crystals which are placed in molds for the manufacture of laminate veneers. Other patents related to laminate veneers are U.S. Pat. Nos. 3,004,343; 3,046,657; 3,327,016; 3,375,582; 3,423,829; 3,423,830; 3,483,618; 3,647,498 and 3,760,502.

SUMMARY OF THE INVENTION

It is a primary feature of the present invention to provide a novel material which is of generally low cost nature and which finds a wide range of effective uses in biological fields such as medicine and dentistry and in mechanical and electromechanical fields as well.

It is an even further feature of the present invention to provide a novel microcellular ceramic material which has a microcellular structure closely approximating the trabecular cellular structure of bone.

It is also an important feature of this invention to provide a novel microcellular ceramic material which incorporates a multiplicity of elongated ceramic fibers or rods which are fused at the lines of contact that are defined with adjacent fibers or rods, thus forming an integrated cellular ceramic log, bundle or mass.

It is an even further feature of this invention to provide a novel microcellular ceramic material which may be efficiently cut either transversely or lengthwise from a bundle or log of fused ceramic fibers to thereby define thin cellular wafers of ceramic material which may be laminated and fused in order to form a useful microcellular object such as a dental or medical prosthesis.

It is also a feature of this invention to provide a novel microcellular ceramic material which may be efficiently utilized in thin wafer form to thus define a heat moldable ceramic dental veneer structure which may be efficiently bonded to the labial surfaces of the teeth of a dental patient.

It is an even further feature of this invention to provide a novel microcellular ceramic material for dental veneers which may be provided with efficient coloring through utilization of selectively colored fibers to thus form microdots of color that blend to form the appearance of dental enamel.

Among the several features of this invention is contemplated the provision of a novel microcellular ceramic material having interstices which may be filled with any one of a number of suitable polymer materials and which may be efficiently utilized for the manufacture of dental veneers and other dental restorations such as crowns, caps, etc.

It is also a feature of this invention to provide a novel microcellular ceramic material which may be utilized to form mechanical structures and which may incorporate electrical conductors as a part thereof in order to provide the mechanical structure with a controlled electrical transmitting characteristic.

Briefly, the present invention involves a microcellular ceramic material wherein the glass from which it is composed is of prismatic, crystalline nature rather than being amorphous. This prismatic or crystalline characteristic is accomplished through a sintering technique taking advantage of the wide range of melting and fusion of a silicate type of material such as silicate glass. It is important and vital that the prisms or crystals be developed over a low range of the melting temperature of the silicate material so that a crystalline structural growth is developed in the material that provides maximum tensile strength, impact resistance and flexibility thereto.

From the standpoint of manufacture, microscopically fine fibers or rods of crystalline vitreous or silaceous materials are arranged with the rods or fibers in side-by-side touching relationship. This can be accomplished by placing the elongated fibers in a tubular receptacle. The mass of fibrous rods is then brought to temperature quickly to achieve fusion at the elongated contact lines or points of the rods. The rods or fibers may be of cylindrical form or, in the alternative, may take other elongated forms without departing from the spirit and scope of the invention. It is important that the fusion temperatures be arrived at in either a high vacuum chamber or in a chamber with inert gases under pressure so that no oxidation or any degeneration of the previous crystalline growth will occur during the fusion process. Immediately after spot or line fusion of the rods to each other to form the microcellular nature of the ceramics, the material must be cooled in such a fashion so as not to disrupt the crystalline nature of the individual rods within the microcellular composite. After spot fusion, the microfine mass of elongated fibers or rods defines interstices or spaces in the mass which provide the mass with a lightweight character. The fused fibrous rod mass, which is also referred to as a log or mass cylinder of the fused microfine fibers, may then be sliced in transverse section or in longitudinal section to develop thin wafers of ceramic material that can be efficiently molded into various configurations and forms. These materials may be layered, depending upon their exact nature and may be infused with various polymer substances which enters into the hollow cellular spaces or interstices created by the spot fusion of the glass fibers or rods.

Depending on the nature of the glass microcellular ceramic and the infused polymer system, these layers of microcellular ceramic materials can be fused or bonded together in either a transverse or a longitudinal fashion and then subjected to various molding procedures to produce structures of medical or dental character or which may be efficiently utilized as structural members in other industrial environments.

An advantage in the manufacture and distribution of microcellular ceramic materials for medical, dental and other uses, is the ready availability of raw materials in virtually all earth environments. Moreover, microcellular ceramic materials are biologically compatible, physiologically inert, chemically inert and exhibit a low degree of biological reaction with bone, muscle and skin tissues of human and other animal patients. Such materials are nontoxic and can be employed in a number of situations such as in replacement of certain bone structure of the human body whether it be of the skull, long bones, joint areas, such as hip joints and tempero-mandibular joints, digital extremities, long bones of the arms or legs, etc. The bio-compatibility and the ability for boney spicules and tissue to infiltrate and to grow within the microcellular spaces or voids between fused fibers or rods is an exceptional advantage to the use of these materials for hip replacement joints, temperomandibular joint replacements, jaws, skull bones, etc., for example, the use of microcellular ceramic material composed of lithium aluminum silicate is exceptional for use as a weight-bearing area in a hip joint. This material, because of its low coefficient of friction and ability toward self-lubrication and its high strength and impact resistance, is an ideal ceramic material for such stress-bearing joint prosthesis.

Another advantage of microcellular ceramic materials in bone replacement prosthesis is that the trabecular pattern that is normally present for stress relief in boney tissues can be prefabricated into such a replacement prosthesis, thereby minimizing or totally eliminating the possibility for having to replace the prosthesis in future years and could well be a totally permanent type of prosthesis that becomes an integral part of the human body for the lifetime of even young individuals.

The method whereby microcellular ceramic material is fabricated is by the use of an appropriate silicate material being drawn into fine microscopic fibers, much as the fibers that are used in the development of the fiber optic devices that are currently in use. These fine microscopic fibers are then packed into bundles such that they lie in side-by-side touching relationship. The bundles of microscopic fibers are first fused at the lines of contact therebetween and are then subjected to a sintering or heat annealing process to produce a crystalline rather than amorphous structure. Following that process, if the fibers are to be filled with polymer material, the fibers are then packed into either heat-vacuum chambers or into inert gas-filled pressure heat chambers and spot fused at the lines of contact between the fibers. The fusion process produces a multifibered microcellular log structure. These logs are capable of being sliced longitudinally or transversely into layers, sheets or wafers which may be of microscopically thin character. Depending upon the different materials from which the silicate or glass or ceramic types of microcellular structures are formed, they can be infused with a polymer system to impart composite characteristics. Layers of polymer infused sheets or wafers of microcellular ceramic material may be oriented in stacked or laminar form and then fused into a cellular laminated mass. Fusion can be accomplished chemically, electronically or with the use of sufficient heat to fuse the laminar layers into a solid laminated mass thereby forming sheets. These laminated sheets of various microcellular ceramics and/or polymers can then be molded into a variety of configurations for use in environments such as in dentistry, medicine, aerospace, etc.

In mechanical industries microcellular ceramic material may be employed in the manufacture of structural members, sheets and other configurations which are intended for use under high stress. For example, in the aerospace industry microcellular ceramic material may be employed for portions of the skin and structural members of an aerospace vehicle. If desired, the microcellular ceramic material may also have controlled electrical and electronic circuitry integrated therein such as by incorporating metal foil or other metal forms which are integrated into the ceramic material. Also, if desirable, the crystals of the microcellular ceramic material may be polarized during the crystallization process to impart certain electronic qualities to the individual wafers or sheets for a variety of electrical and electronic purposes.

The microcellular ceramic material may also incorporate combinations of acid soluble glass fibers together with acid resistant glass fibers. When a log of such materials is cut transversely, the exposed surface is capable of being acid etched to dissolve the superficial portions of the acid soluble glass fibers, thus forming surface irregularities that promote efficient bonding of the microcellular ceramic material to materials of like or different nature. For example, in the manufacture of dental veneers composed of microcellular ceramic materials an inner layer of the veneer may be composed of a lamination having acid soluble and acid resistant glass members. The inner surface of the ceramic veneer may then be acid etched to develop an efficient bonding surface. The dental veneer will then be capable of efficient bonding to the enamel surface of a tooth to which it is to be attached. The other laminations of the dental veneer will, in this case, typically be composed of said insoluble crystalline glass for optimum characteristics of wear resistance, color stability and resistance to staining.

Other and further objects and features of the present invention will become obvious to one skilled in the art upon an understanding of the following specification.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings, which drawings form a part of this specification.

It is to be noted, however, that the appended drawings illustrate representative structural relationships that are made possible by employment of the method and materials set forth herein and are therefore not to be considered limiting of the scope of the invention, for the invention may admit to other equally effective embodiments without departing from the spirit and scope thereof.

IN THE DRAWINGS

FIG. 1 is an isometric illustration of a dental laminate veneer having the center and lower portions cut away to show three laminations of microcellular ceramic material which are in fused assembly to form the laminate veneer.

FIG. 2 is a sectional view of a number of glass rods or fibers which are positioned in side-by-side touching relation and which are shown prior to sintering thereof to form a microcellular log mass.

FIG. 3 is a transverse sectional view similar to that of FIG. 2 and illustrating the slightly modified configuration of the glass fibers or rods which is achieved by the sintering process.

FIG. 4 is an isometric illustration of an elongated chamber filled with ceramic rods or fibers, which chamber is of generally cylindrical form, thereby orienting the rods or fibers in side-by-side touching relation such as shown in FIG. 2.

Figure 5:
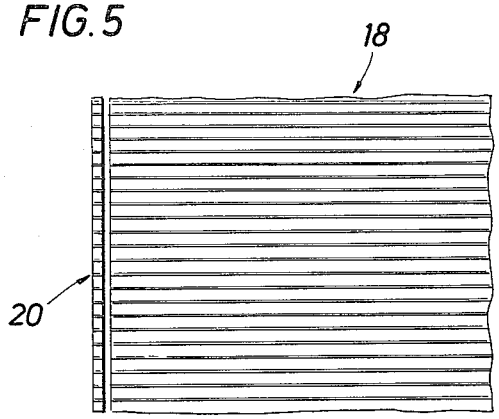

FIG. 5 is a side view of an elongated log of sintered ceramic rods or fibers such as it would appear after having been removed from the elongated chamber of FIG. 3 and further showing slicing of the log transversely to achieve a thin wafer of microcellular ceramic material.

Figure 6:
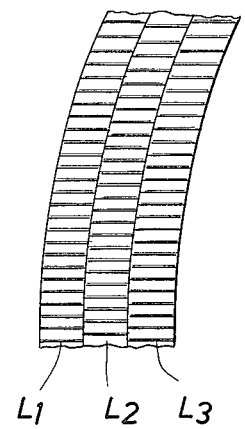

FIG. 6 is a fragmentary sectional view of multiple layers of microcellular ceramic material such as illustrated by the sheet shown in FIG. 4, which layers are shown to be formed to a curved configuration and sintered into laminar form such as would be the case in the manufacture of microcellular ceramic laminate dental veneer of FIG. 1.

Figure 7:
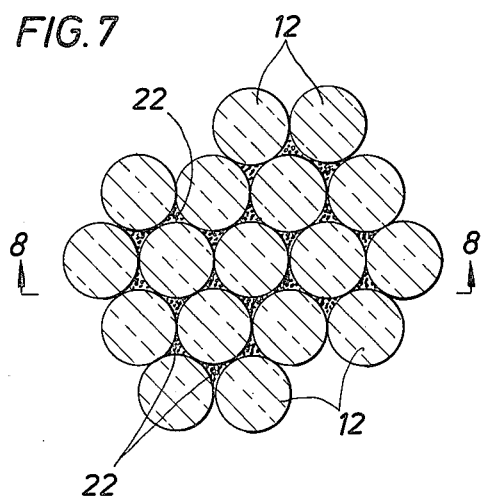

FIG. 7 is a partial transverse sectional view of microcellular ceramic material illustrating incorporation of fibers of colored or acid soluble ceramic material in the interstices defined by the primary ceramic rods or fibers.

Figure 8:
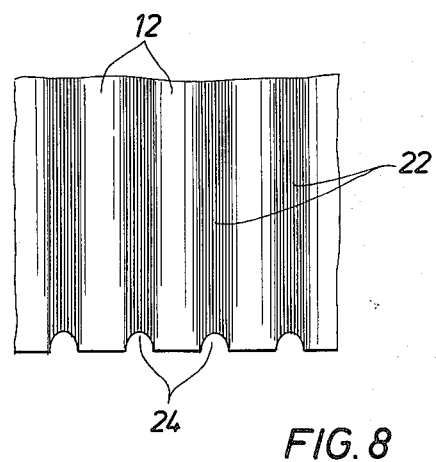

FIG. 8 is a partial sectional view taken along line 8—8 of FIG. 6 and illustrating the development of an irregular surface configuration by acid etching when acid soluble ceramic fiber materials are employed in the interstitial spaces such as shown in FIG. 6.

Figure 9:
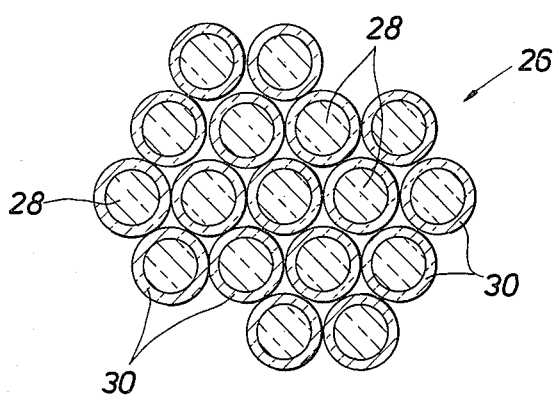

FIG. 9 is a transverse sectional view of a modified embodiment of the present invention incorporating glass rods or fibers each being clad with a glass of different composition.

Figure 10:
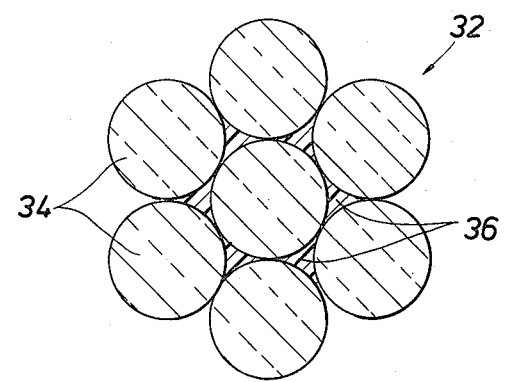

FIG. 10 is a transverse sectional view of a further modified embodiment of the invention incorporating polymer material in the interstices of the microcellular ceramic material.

DETAILED DESCRIPTION OF PREFERRED EMBODIMENT

Referring now to the drawings and first to FIG. 1, a microcellular ceramic dental veneer is shown generally at 1 which includes three layers or laminations 2, 3 and 4 which are fused in integral assembly. The outer layer 2 and the inner layer 4 may be composed of the same, similar or different ceramic compositions depending on the characteristics that are desired. For example, the inner layer 4 may be efficiently composed for bonding to the enamel surface of a tooth. The middle lamination 3 may be provided with a color system to provide the veneer with a natural tooth-like appearance. The outer layer 2 may be particularly composed for efficiency of wear resistance, resistance to staining, energy absorption, etc.

Referring now to FIG. 2, a bundle of ceramic fibers is illustrated generally at 10 which incorporates a multiplicity of elongated generally cylindrical ceramic fibers or rods 12 which are placed in side-by-side relationship, thereby defining lines of contact along the length thereof. These elongated rods or fibers 12 define interstitial spaces 14 therebetween, which spaces may be void as shown in FIG. 1 or, in the alternative, may be filled or partially filled with a polymer or ceramic or metallic fibers or a combination of both, such as in the manner generally shown in FIG. 6. In order to form a microcellular ceramic object of integral structure, the elongated fibers or rods 12 are sintered along the lines of contact thereof in the manner shown in FIG. 3, thereby causing the individual fibers to be slightly deformed at the lines of contact, thereby rendering them from the cylindrical configuration of FIG. 2 to a substantially pentagonal, hexagonal or octagonal configuration such as shown in FIG. 3. It is desirable that substantial interstitial spaces remain between the individual rods or fibers such as shown in FIG. 3 to thereby permit the resulting integral ceramic object to be of microcellular structure.

In order to form the ceramic or glass fibers of FIG. 2 to the fused, integrated form of FIG. 3, a multiplicity of the ceramic fibers is placed within an elongated chamber such as the elongated cylindrical chamber 16 of FIG. 4. The ceramic fibers 12 are packed tightly within the chamber 16 to thereby ensure the development of an adequately touching relationship between the fibers along the length thereof. The fusion chamber 16 is then subjected to a heat temperature significantly high to cause fusion of the individual glass fibers at line contact therebetween but not sufficiently high to induce melting of the entire glass fiber. It is very critical that the temperature be such that the glass or the silicate or silaceous material have spot fusion or linear fusion at the points or lines of contact between the individual glass fibers. After the fusion process has occurred, the temperature is then lowered to an annealing temperature to allow the individual glass fibers to crystallize and thus form a crystalline fibrous microcellular ceramic structure. It is important that the microcellular ceramic material be rendered to crystalline structure rather than being of amorphous nature. The crystalline microcellular ceramic structure provides the material with flexibility and energy absorbing capability. On the other hand, an amorphous ceramic structure is of brittle nature and is relatively inflexible. An amorphous ceramic structure also is quite incapable of absorbing energy.

The process of manufacture could be organized in generally reverse manner wherein the individual ceramic fibers are crystallized prior to fusion of the glass rods or fibers together to form an integral microcellular ceramic structure. This manufacturing process would be quite critical from the standpoint of temperature range. If the temperature is brought too high, the crystallization or annealing of the individual glass fibers would be damaged and there would be improper fusion of the glass rods. The preferred process is an initial fusion of the glass rods to form a microcellular ceramic structure, followed by an annealing or crystallization process thereby causing the various glass fibers of the mass to become crystalline after the rods or fibers have been fused.

After fusion and crystallization of the fibers has been accomplished, the general form of the resulting microcellular ceramic object will be a log structure which is generally shown at 18 in FIG. 5. The microcellular ceramic log may then be sectioned as shown at the left-hand portion of FIG. 5 such as by cutting the log transversely with a diamond saw or the like to thereby yield thin sheets of microcellular ceramic material such as shown generally at 20. These thin sheets of microcellular material then may be employed for the formation of other mechanical structures such as medical or dental structures such as bone prosthesis, dental veneers, etc., or various mechanical structures such as ball and socket hip joint prosthesis, structural members and vehicle skin for the aerospace industry or for the manufacture of automobile parts and for a wide variety of other uses.

In one suitable example, as shown in FIG. 6, thin sheets of microcellular ceramic material such as shown generally at 20 in FIG. 5 may be laminated into formed and bonded assembly in the manner shown in the fragmentary view of FIG. 6. FIG. 6 is a sectional view such as might be taken through a portion of a microcellular ceramic laminate dental veneer that is intended for bonded attachment to the labial surfaces of the teeth of a dental patient as shown in FIG. 1. The various interstices of each of the layers of the microcellular ceramic laminate veneer such as shown at L1, L2 and L3 of FIG. 6 may be filled with a wide variety of materials to accomplish intended results. For example, in one form of the invention, the interstices between the individual ceramic fibers 12 may be filled or substantially filled with other fibers of ceramic material. In order to provide a laminate ceramic veneer with the color and other visual characteristics of a natural tooth, the ceramic fibers 22 disposed in the interstitial spaces may be colored so as to provide desired overall color characteristics. The individual glass fibers in the interstitial spaces, upon transverse slicing of a microcellular ceramic log may be colored and oriented so as to define microdots of color in the various veneer wafers or laminations. The veneer wafers or laminations may be cross-sectioned in the order of 1/10 millimeter thick from bundles by cross cutting the bundle with a diamond saw. By controlling the colors of the core and jacket glasses of the bundles, the result will be a glass form having microdots of color. An additive color system may be employed (such as in the manner of the blue, red, green dots of a color television screen). The enamel part of the laminate veneer may be provided with fluorescent materials in the interstitial spaces so that when light rays strike the fluorescent materials, the fluorescence becomes excited and emits more light than it has received. Underneath, in other layers, subtractive colors may be employed such as yellow, cyan, magenta, which may also be dispersed in microdot form to thereby function as filters through which the light passes. A color subtractive system of this nature develops a background color effect and thereby provides the laminate veneer with color in depth to thus provide the visual effect of a normal tooth. The additive and subtractive color systems which would be developed in these layers of additive and subtractive color in microdot form cooperate to provide a dental veneer having the normal color and subtle translucent effect of a normal tooth. The color systems may be employed in selected layers of the dental veneer and in selected areas of selected layers to promote the desired visual effect.

In another form of the invention, the fibers of glass disposed within the interstitial spaces such as shown in FIG. 6 may be composed of an acid soluble glass while the primary rods or fibers 12 of the microcellular ceramic log or bundle may be composed of acid insoluble glass. This type of microcellular ceramic material may form the inner layer L3 of a laminate dental veneer such as shown in FIG. 6 or the layer 4 of FIG. 1. After the laminate veneer has been completely assembled and fused to form a multilayered veneer system such as shown in FIG. 6, an acid would be brought into contact with the inner surface of the veneer causing the end portions of the acid soluble rods to become dissolved in the manner shown at 24 in FIG. 8. When this is done, the inside surface of the laminate veneer will be of irregular form as shown at the lower portion of FIG. 8. This inside surface, being of irregular form will readily accept a bonding material, thereby enabling the laminate veneer to be efficiently bonded to the enamel surface of a patient's tooth. Of course, the enamel surface will also be prepared by acid etching to render it of similar irregular form, thereby preparing the enamel to efficiently receive bonding material.

Microcellular ceramic material may take many suitable forms, depending upon the characteristics that are ultimately desired. One suitable type of microcellular ceramic material may take the following form. Microfibers of glass in the order of 10 microns to 25 microns in diameter may be brought into assembly in the manner shown in FIG. 2. The primary fibers or core glass may be composed of a flint glass such as manufactured by American Optical Company in a form having code number F-2. The individual fibers may be provided with a jacket glass or cladding glass such as glass manufactured by American Optical Company having a code number R-6. When these types of glasses are employed in the development of a microcellular ceramic material, the fusion temperature range will be in the order of 900° F. to 1100° F. The molding temperature will be in the order of 750° F. thereby defining a significantly wide range of temperature, i.e., between 750° F. and 900° F. within which the material can actually be molded. Fusion of the multiple layers would require a temperature range in the order of between 900° F. and 1100° F.

There are some glasses that can be used at lower temperatures but the flint glass adequately meets a specification generally designated for the manufacture of laminate veneers for dental application. The flint glass is manufactured by the Schott Glass Company. These glass fibers are arranged in bundles such as shown in FIGS. 4 and 5, which bundles may incorporate different varieties of glass organized in any suitable form. For example, primary fibers of flint glass may be employed with several smaller fibers formed of acid soluble glass being disposed in the interstitial spaces between the flint glass fibers. When these different kinds of glasses are fused together, there is developed a bundle or log of microfibers which are fused together thereby yielding a basic cross-sectional configuration which is of solid form with acid soluble glass generally disposed in partially surrounding relation with each fiber of insoluble glass. These immiscible glasses remain segregated to the extent that they do not mix but the immiscible glasses are capable of being sintered together to form an integral assembly. Wafers or sheets are then cut from the log or bundle of acid soluble and acid insoluble glasses. These wafers or sheets are then subjected to an acid bath and the acid soluble glass is dissolved to such extent that all or portions of the interstitial spaces are cleared, thereby yielding a porous wafer. In the manufacture of dental laminate veneers this porous layer may form the inner lamination of the laminate veneer, such as shown at 4 in FIG. 1, thereby providing an irregular surface which is capable of efficient bonding to the enamel surface of the patient's tooth. Other layers of the laminate veneer may be composed of acid insoluble glasses of different characteristics. For example, different glass fibers of different color characteristics may be employed to provide the lamination with a particular color characteristic. By superposing different colored laminations of microcellular ceramic material in organized fashion, a laminate veneer can be developed having the color characteristics of a normal tooth. Moreover, the color of the tooth will be permanent and the tooth will not tend to become stained or take on different color characteristics after being in the oral cavity for extended periods of time.

In another form of the invention, as shown in FIG. 9, each of the various fibers of a microcellular ceramic fiber bundle or log may be composed of glass fibers having a central core and an external cladding or configuration of a different glass material. For example, each of the various fibers of the log or bundle may be provided with a fine central core 28, such as may be composed of a flint glass such as that manufactured by the Schott Glass Company and sold under designation F-2. This glass is a flint glass which is drawn to a fine fiber. The flint glass is then provided with a cladding or jacket composed of glass manufactured by the Schott Glass Company and designated R-6. The cladding glass functions as an internal reflector for reflecting light. The light will then follow down each fiber because the R-6 cladding glass has a different index of refraction as compared to the glass forming the core 28. The cladding glass 30 functions as a reflector to reflect the light waves, so with a core glass composed of the F-2 glass material of the Schott Glass Company and with a cladding or jacket glass of R-6 composition surrounding each of the core fibers 28, the jacketed or clad core will guide or contain light waves and cause them to transmit throughout the length of the fiber. The core and jacket may be composed of any suitable color, to provide the composite glass bundle with particular color characteristics. For example, the cladding glass 30 may be colored in any suitable manner while the core glass 28 may be clear or alternatively colored to achieve desired color characteristics.

Regardless of the desired characteristics of the microcellular ceramic material, it is manufactured in much the same way. The rods or fibers of ceramic material are placed in an appropriate chamber and are brought rather quickly to fusion temperature, such as in the order of 900° F. to 1100° F. in order to accomplish fusion at the interfaces between the fibers. The fused glass bundle is then slowly cooled to the crystallizing temperature, which is maintained for a sufficient period of time to accomplish efficient crystallization. The log of ceramic fibers is then sliced and the slices are subsequently utilized in molding operations. The slices or layers of microcellular ceramic material are then placed in a suitable mold. At a temperature range of from 650° F. to 700° F. the glass layers begin to mold. After they have been properly molded to the desired configuration, the heating range is then raised to a range of 900° F. to 1100° F. to cause fusion at the interfaces of the layers. After fusion has been accomplished, the molded microcellular ceramic material is then slowly cooled to the sintering temperature of the glass. This sintering temperature is maintained sufficiently to cause crystallization of the glass so that the result is a crystalline rather than amorphous type glass structure. If desired, a high fusion glass such as lithium aluminum silicate may be employed in conjunction with controlled fusion and sintering or annealing temperatures for the manufacture of various mechanical structures of crystalline microcellular composition.

In another form of the invention, as shown in FIG. 10, a combination ceramic structure of the microcellular form may be developed having glass fibers similar to those shown in FIGS. 2, 3 and 7, with the interstitial spaces between the fibers being filled with any one of a number of suitable polymer materials. This technique basically involves the use of a glass system of silicon or silicate nature such as lithium aluminum silicate, silicon nitride or silicon carbide or any one of a number of silaceous type materials that are readily available. These materials can be readily extruded or molded or crystallized during a heat annealing process such as that described above. The resin systems that may be employed may be of an epoxy type resin system such as a diacrylate or an epoxy such as a bis phenol-A or a bis GMA type of system. The bis GMA is a a diacrylate and bis phenol-A is one example of an epoxy system which would be a suitable filler for the microcellular ceramic material. These examples, however, are not to be considered limiting of the scope of the invention, it being obvious that any suitable polymer material may be employed to fill the interstitial spaces defined between the glass rods or fibers of the microcellular ceramic material.

In the manufacture of microcellular ceramic material glass fibers may be in the order of 4 microns or less in diameter and can be as large as 10 microns in diameter or as small as 1 micron. The ideal size of these fibers would be in the order of 4 microns in diameter. After fusion of the glass fibers to form a microcellular ceramic structure the resulting microcellular log will then be infused with a polymer resin such as an epoxy. The polymer resin would provide the log with structural integrity, enabling it to be cut into very thin wafers or segments such as by means of a diamond saw. These individual layers or wafers could then be readily shaped to any form and stacked on top of each other to form a composite mass. As shown in FIG. 10, the resulting log of microcellular ceramic material shown generally at 32 incorporates ceramic fibers 34 which are fused together to form an integral assembly. The interstitial spaces between the glass fibers 34 are then filled with a polymer material 36 in the manner described above.

Microcellular ceramic material constructed in accordance with the present invention is effective in the medical environment, especially in orthopedics. A microcellular structure of this nature which closely resembles the trabecular microstructure of bone tissue could be efficiently employed for example in the development of artificial hip joints, vertebrae in the spinal column or artificial substitutes for the bones in arthritis type cases, for example, knuckles, long bones in the hand, digits, etc.

It is also envisioned that a microcellular or trabecular structure of a ceramic or glass or polymer-glass combination, polymer-ceramic combination, for example, could be used for bone replacement of the type described above as well as for replacement of the various bones in the skull, maxilla or mandible in dentistry or in the tempero-mandibular joint in the condile of the templar-mandibular joint.

In the place of dental restorations, not only could the microcellular structures be used for the development of laminate veneer restorations but it could also be efficiently used for the development of traditional dental restoration configurations of a crown or a cap where it could be placed over a prepared tooth surface. Traditionally, the crowns or caps that are placed over a prepared tooth are composed of an amorphous ceramic that is built up by hand with powders and then fused in the oven by either one, two or three bakings at various temperatures to cause fusion of the silicon or the glass materials. The present invention effectively provides for elimination of the very time consuming and painstaking process that is ordinarily accomplished by a dental technician or ceramist.

The concept of the present invention may be effectively employed in conjunction with a wide variety of glass, ceramic and polymer materials. The various molding, fusion and sintering temperatures will depend upon the type of ceramic material that is employed.

In view of the foregoing, it is respectfully submitted that the present invention is one well adapted to attain all of the objects and features hereinabove set forth, together with other features which will be apparent from a description of the apparatus and method set forth herein. It will be understood that certain combinations and subcombinations are of utility and may be employed without reference to other features and subcombinations. This is contemplated by and is within the scope of the present invention.

As many possible embodiments may be made of this invention without departing from the spirit or scope thereof, it is to be understood that all matters hereinabove set forth or shown in the accompanying drawings are to be interpreted as illustrative and not in a limiting sense.

What is claimed is:

1. A thin microcellular ceramic laminate dental veneer for attachment to the labial surfaces of the teeth of a dental patient, said veneer comprising:
   a multiplicity of fibers composed of crystalline ceramic material, said crystalline ceramic fibers being positioned in side-by-side, generally parallel relation establishing lines of contact with adjacent fibers along the length thereof, said fibers being heat fused to adjacent fibers at the lines of contact therebetween to form a porous mass, said ceramic fibers collectively defining a thin tooth shaped layer surface of said laminate veneer for covering the labial surface of a human tooth.

2. A microcellular ceramic dental laminate veneer as recited in claim 1 wherein:
   (a) said laminate veneer is formed by at least two layers each being formed by said ceramic fibers in fused assembly; and
   (b) said layers are fused in integral surface-to-surface assembly with the fibers of each layer in substantially end-to-end relation to thus define said laminate veneer.

3. A microcellular ceramic laminate dental veneer as recited in claim 2, wherein:
   said layers of fibers are selectively provided with dental color systems to provide the laminate dental veneer with the color and appearance of a normal tooth.

4. A microcellular ceramic laminate dental veneer as recited in claim 3, wherein:
   at least one of said layers of said fibers incorporates selectively interspersed colored fibers of crystalline ceramic material.

5. A microcellular ceramic laminate dental veneer as recited in claim 4, wherein:
   said interspersed colored fibers of crystalline ceramic material selectively define additive and subtractive color systems in selected layers of said laminate dental veneer.

6. A microcellular ceramic laminate dental veneer as recited in claim 2, wherein:
   (a) at least one of said layers of said laminate veneer is composed of primary crystalline ceramic fibers being positioned in side-by-side touching relation and defining interstitial spaces therebetween; and
   (b) a matrix filling said interstitial spaces and cooperating with said primary crystalline ceramic fibers to form a laminate veneer of integral character.

7. A microcellular ceramic laminate dental veneer as recited in claim 6, wherein said filling means comprises:
   secondary ceramic fibers which are soluble when exposed to a selective fluid medium, said primary fibers being insoluble to said fluid medium, and upon exposing a surface comprising the exposed ends of said insoluble primary fibers and soluble secondary fibers, portions of the secondary fibers are dissolved, exposing the interstitial spaces at said exposed surface, thereby rendering said exposed surface to a roughened characteristic prepared for efficient reception of bonding material.

8. A microcellular ceramic laminate dental veneer as recited in claim 6, wherein said filling means comprises:
   a plurality of secondary crystalline ceramic fibers positioned in side-by-side touching relation, said secondary fibers being of smaller cross-sectional dimension as compared to the cross-sectional dimension of said primary fibers.

9. A microcellular ceramic laminate dental veneer as recited in claim 8 wherein:
   said secondary fibers are of selective color to provide said laminate dental veneer with the appearance of a normal tooth.

10. A microcellular ceramic laminate veneer as recited in claim 1, wherein:
    said laminate veneer surface forms an outer surface and an inner surface, said inner surface being prepared for efficient bonding thereof to the enamel surface of a patient's tooth.

11. A microcellular ceramic laminate veneer as recited in claim 1, wherein:
    (a) said ceramic laminate veneer has an outer surface and an inner surface, said inner surface being prepared for bonding to the enamel surface of a patient's tooth; and
    (b) said inner and outer surfaces are defined collectively by the end surfaces of said fibers.

12. A microcellular ceramic laminate dental veneer as recited in claim 11, wherein:
    said filling means is composed of a polymer material.

13. A microcellular ceramic laminate dental veneer as recited in claim 1, wherein:
    (a) said ceramic laminate veneer has an outer surface and an inner surface, said inner surface being prepared for bonding to the enamel labial surface of a patient's tooth; and
    (b) said inner and outer surfaces are defined collectively by the side surfaces of surface exposed ones of said fibers.

14. A microcellular ceramic laminate dental veneer as recited in claim 1, wherein:
    said crystalline ceramic fibers each incorporate a core fiber of crystalline ceramic material having cladding fiber material of crystalline ceramic surrounding said core fiber and forming the outer surface of said ceramic fiber.

15. A microcellular ceramic laminate dental veneer as recited in claim 14, wherein:
    said core fiber material and cladding fiber material are of different ceramic comosition.

* * * * *